United States Patent [19]

Iemura et al.

[11] Patent Number: 4,603,130
[45] Date of Patent: * Jul. 29, 1986

[54] 1-SUBSTITUTED-2-(PIPERAZINYL OR HOMOPIPERAZINYL)-BENZIMIDAZOLE COMPOUNDS AND PHARMACEUTICAL COMPOSITION

[75] Inventors: Ryuichi Iemura, Kawanishi; Tsuneo Kawashima; Toshikazu Fukuda, both of Osaka; Keizo Ito, Osaka; Takashi Nose, Nara; Goro Tsukamoto, Toyonaka, all of Japan

[73] Assignee: Kanebo, Ltd., Tokyo, Japan

[*] Notice: The portion of the term of this patent subsequent to Feb. 7, 2001 has been disclaimed.

[21] Appl. No.: 594,298

[22] Filed: Mar. 28, 1984

[30] Foreign Application Priority Data

Apr. 27, 1983 [JP] Japan ................................ 58-75178

[51] Int. Cl.$^4$ ................. C07D 403/04; C07D 241/02; A61K 31/55; A61K 31/495
[52] U.S. Cl. .................................... 514/218; 544/370; 260/245.6; 514/253
[58] Field of Search ........................ 544/370; 424/250; 260/245.6; 514/218, 253

[56] References Cited

U.S. PATENT DOCUMENTS

| | | |
|---|---|---|
| 3,423,413 | 1/1969 | Priewe et al. ........................ 544/370 |
| 3,658,822 | 4/1972 | Fauran et al. ....................... 544/370 |
| 3,794,651 | 2/1974 | Helsley et al. ...................... 544/370 |
| 4,011,322 | 3/1977 | Rahtz et al. ........................ 544/370 |
| 4,029,789 | 6/1977 | Fauran et al. ....................... 544/370 |
| 4,093,726 | 6/1978 | Winn et al. ......................... 544/370 |
| 4,179,505 | 12/1979 | Raeymakers et al. ................. 544/370 |
| 4,430,343 | 2/1984 | Iemura et al. ....................... 544/370 |
| 4,459,296 | 7/1984 | Ancher et al. ....................... 544/370 |

FOREIGN PATENT DOCUMENTS 1216381 12/1970 United Kingdom ................ 544/370

OTHER PUBLICATIONS

Pharmaprojects, Therapeutic Categories, vol. 4, May 1983, R8A ar14.
Pharmaprojects, Therapeutic Categories Update, Apr. 1983, au 75 R8A.

Primary Examiner—George F. Lesmes
Assistant Examiner—S. A. Gibson
Attorney, Agent, or Firm—Wegner & Bretschneider

[57] ABSTRACT

Novel benzimidazole derivatives of the formula:

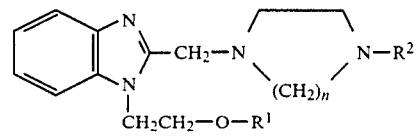

wherein $R^1$ is a lower alkyl group, a lower alkenyl group or a lower alkynyl group, $R^2$ is hydrogen atom, a lower alkyl group or a lower hydroxyalkyl group, and n is 2 or 3, or a pharmaceutically acceptable acid addition salt thereof, which have potent antihistaminic activity with less toxicity and hence are useful as an antihistaminics, and a process for the preparation of the compounds, and a pharmaceutical composition useful as antihistaminics containing the compound as an essential active ingredient.

8 Claims, No Drawings

1-SUBSTITUTED-2-(PIPERAZINYL OR HOMOPIPERAZINYL)-BENZIMIDAZOLE COMPOUNDS AND PHARMACEUTICAL COMPOSITION

The present invention relates to novel benzimidazole derivatives, a process for the preparation thereof and a pharmaceutical composition containing the compound as an essential active ingredient. More particularly, it relates to benzimidazole derivatives of the formula:

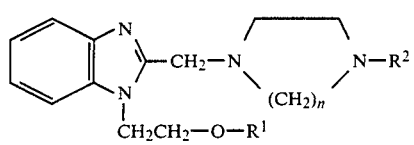

wherein $R^1$ is a lower alkyl group, a lower alkenyl group or a lower alkynyl group, $R^2$ is hydrogen atom, a lower alkyl group or a lower hydroxyalkyl group, and n is 2 or 3, or a pharmaceutically acceptable acid addition salt thereof, and a process for the preparation thereof, and a pharmaceutical composition useful as antihistaminics containing the compound as an essential active ingredient.

There have hitherto been developed various anti-histaminics, for example, chlorpheniramine maleate and homochlorcyclizine hydrochloride, but these known anti-histaminics are not necessarily satisfactory because some of them have comparatively weak activity; some of them show undesirable side effect such as hypnotic activity, while show potent antihistaminic activity; or some of them show comparatively high toxicity.

U.S. Pat. No. 3,423,413 discloses benzimidazole derivatives of the following formula, which have anti-allergic activity and anti-inflammatory activity:

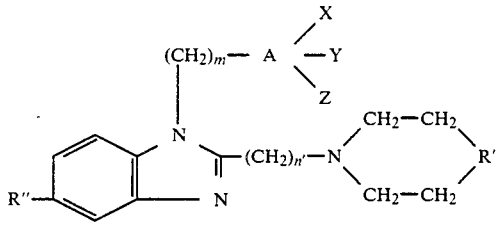

wherein Ⓐ is a ring selected from the group consisting of benzene and pyridine rings; X, Y, Z are members of the group consisting of hydrogen, halogen having an atomic weight of less than 100, hydroxyl, lower alkoxy, lower alkanoyloxy, lower alkoxy(lower)alkoxy, and the nitro radical; m is an integer between zero and two; n' is an integer between one and three; R' is a member of the group consisting of oxygen and N—R''' wherein R''' is a member of the group consisting of hydrogen, lower alkyl, lower hydroxyalkyl, lower alkanoyl(lower)hydroxyalkyl, phenyl(lower)alkyl, and lower alkoxy(lower)alkyl; and R'' is a member of the group consisting of hydrogen, halogen having a molecular weight of less than 100, and lower alkoxy, among which 1-(4-fluorobenzyl)-2-[4-(2-hydroxyethyl)-1-piperazinyl]methylbenzimidazole (Compound A) of the following formula has the most potent anti-allergic activity.

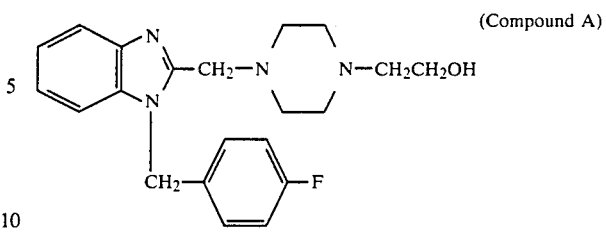

However, the compounds (I) of the present invention are different from the compounds disclosed in the above U.S. patent, because the compounds (I) of the present invention has an ether bond-containing group, i.e. a lower alkoxyethyl group, a lower alkenyloxyethyl group or a lower alkynyloxyethyl group at 1-position of benzimidazole nucleus. Moreover, the compounds of the present invention are superior to Compound A in protecting activity against histamine-induced lethality according to experiment in guinea pig as described hereinafter.

The present inventors have extensively studied on a new type of antihistaminics having potent antihistaminic activity with less side effect and low toxicity, and as a result, it has been found that the novel benzimidazole derivatives of the formula (I) having a specific chemical structure have satisfactory properties.

An object of the present invention is to provide novel benzimidazole derivatives and a pharmaceutically acceptable acid addition salt thereof. Another object of the invention is to provide compounds which have potent histamine antagonistic activity with low toxicity and hence are useful for prophylaxis and treatment of various allergic diseases induced by histamine. A further object of the invention is to provide a process for the preparation of said novel benzimidazole derivatives or a pharmaceutically acceptable acid addition salt thereof. A still further object of the invention is to provide an antihistaminics containing as an active ingredient said compounds. These and other objects and advantages of the present invention will be apparent to persons skilled in the art from the following description.

In the present specification, the term "lower alkyl group" denotes an alkyl group having 1 to 3 carbon atoms, such as methyl, ethyl or n-propyl group. The term "lower alkenyl group" denotes an alkenyl group having 2 to 3 carbon atoms, such as vinyl or allyl group. The term "lower alkynyl group" denotes an alkynyl group having 2 to 3 carbon atoms, such as propargyl group. The term "lower hydroxyalkyl group" denotes a hydroxyalkyl group having 1 to 3 carbon atoms in the alkyl moiety, such as hydroxymethyl or hydroxyethyl group.

The pharmaceutically acceptable acid addition salts of the compounds (I) include hydrochloride, sulfate, maleate, fumarate, or the like.

The compounds (I) and their salts of the present invention can be prepared by various processes, for example, by the following processes A, A' and B.

[Process A]

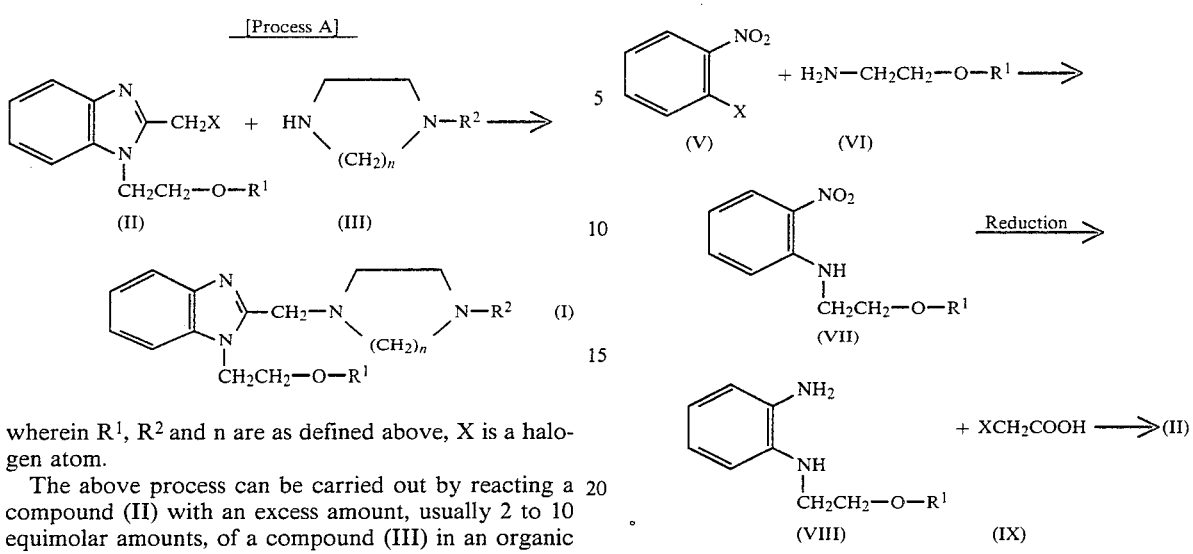

wherein R¹, R² and n are as defined above, X is a halogen atom.

The above process can be carried out by reacting a compound (II) with an excess amount, usually 2 to 10 equimolar amounts, of a compound (III) in an organic solvent at a temperature of from 0° C. to the boiling point of the solvent. Suitable examples of the organic solvent are benzene, toluene, methanol, ethanol, dioxane, N,N-dimethylformamide, dimethylsulfoxide, or the like.

When a compound of the formula (I) wherein R² is hydrogen atom is obtained by the above Process A, it can also be converted into a compound of the formula (I) wherein R² is a lower alkyl group or a lower hydroxyalkyl group by the following Process A':

[Process A']

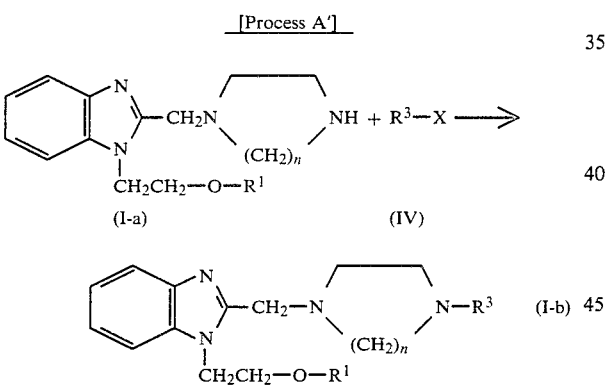

wherein R¹, n and X are as defined above, and R³ is a lower alkyl group or a lower hydroxyalkyl group.

The above process can be carried out by reacting a compound (I-a) with an equimolar or slightly excess amount, usually 1 to 1.5 equivalent amount, of a halogenated compound (IV) in an organic solvent in the presence of a base, optionally in the presence of a catalyst (e.g. potassium iodide). Suitable examples of the organic solvent are chloroform, methanol, or ethanol. The base includes alkali metal salts (e.g. sodium hydrogen carbonate, potassium carbonate), or organic bases (e.g. triethylamine, pyridine). The base is preferably used in an amount of 1 to 1.5 mole to 1 mole of the compound (I-a). The reaction is usually carried out at a temperature of from room temperature to a boiling point of the organic solvent.

The starting compound (II) used in the above Process A can be prepared, for example, by a process as shown in the following reaction scheme:

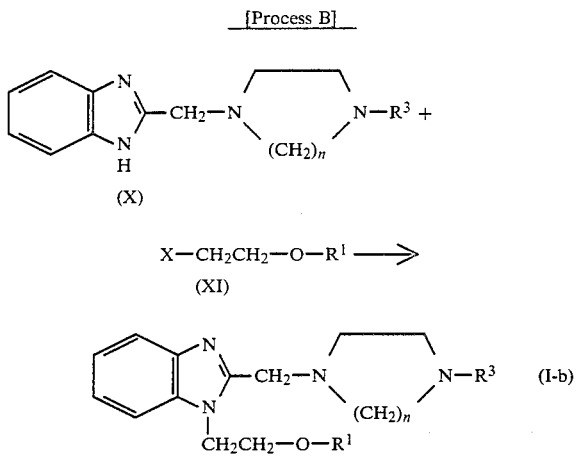

wherein R¹ and X are as defined above.

The above process is carried out as follows. Firstly, o-nitrohalobenzene (V) is reacted with stirring with 2 to 3 equivalents of an amine (VI) at 100° to 200° C. in the presence or absence of a solvent to give a compound (VII). When the reaction is carried out in a solvent, there is used a solvent such as toluene, xylene, n-propanol, n-butanol, N,N-dimethylformamide. The compound (VII) thus obtained is reduced by zinc-sodium hydroxide, stannous chloride-hydrochloric acid, or by catalytic hydrogenation in the presence of a catalyst such as, palladium-carbon to give a compound (VIII). The compound (VIII) is reacted with a halogenated acetic acid (IX) in hydrochloric acid with heating to give the desired compound (II).

Alternatively, the compound (I) wherein R² is a lower alkyl or a lower hydroxyalkyl, i.e. the compound (I-b) can be prepared by in the following Process B:

[Process B]

$$\text{(X)} \quad + $$

$$X-CH_2CH_2-O-R^1$$
(XI)

$$\longrightarrow \text{(I-b)}$$

wherein R¹, R³, n and X are as defined above.

The above process can be carried out by reacting a compound (X) with an equimolar or slightly excess amount, usually 1 to 1.5 equivalent, of a halogenated compound (XI) in an organic solvent in the presence of a base, and optionally, in the presence of potassium iodide. Suitable examples of the solvent are methanol, ethanol, N,N-dimethylformamide, and dimethylsulfoxide. The base includes an alkali metal (e.g. sodium metal), or an alkali metal hydride (e.g. sodium hydride, potassium hydride).

The starting compound (X) used in the above Process B can be prepared by the following process:

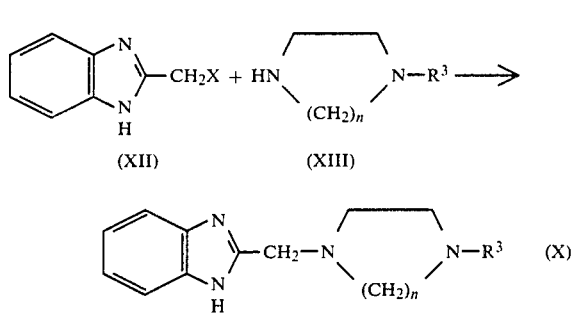

wherein $R^3$, n and X are as defined above.

The reaction of a compound (XII) and a compound (XIII) in the above process is carried out under the same reaction conditions as in the reaction of the compound (II) and the compound (III) in the above Process A.

The compound (I-a) can also be prepared in the same manner as in the above Process B, followed by removal of the N-substituent as shown in the following reaction scheme:

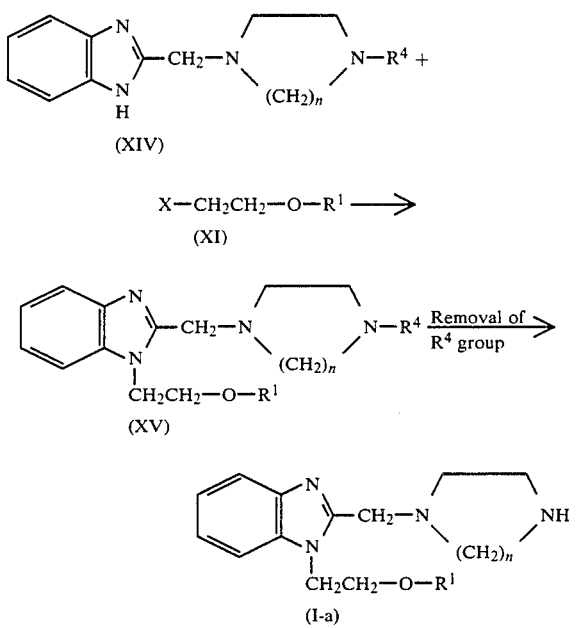

wherein $R^1$, n and X are as defined above, and $R^4$ is a protecting group which can be removed by catalytic reduction or under an acidic or basic condition.

The above process can be carried out by reacting a compound (XIV) and a compound (XI) under the same reaction conditions as in the reaction of the compound (X) and the compound (XI) in Process B to give a compound (XV), followed by removing the protecting group on the compound (XV) by a conventional method. The protecting group as defined for $R^4$ includes, for example, a benzyl group which can easily be removed by a conventional catalytic reduction, and a formyl or ethoxycarbonyl group which can easily be removed under an acidic or basic condition.

The starting compound (XIV) used in the above process can be prepared by the process as shown in the following reaction scheme:

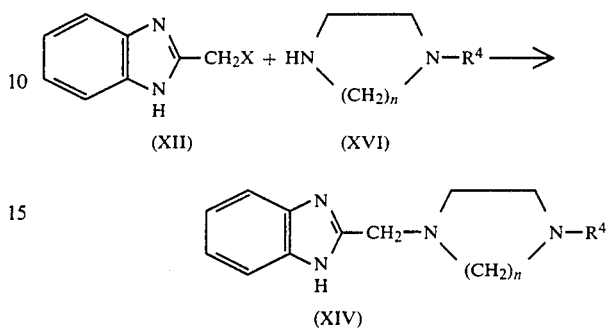

wherein $R^4$, n and X are as defined above.

The above process can be carried out by reacting a compound (XII) and a compound (XVI) under the same reaction conditions as in the reaction of the compound (XII) and the compound (XIII) as mentioned hereinbefore.

The compounds (I) obtained in the form of a free base by the above processes can be converted into their acid addition salts by a conventional method, for example, by treating the free base with an inorganic acid (e.g. hydrochloric acid, sulfuric acid), or an organic acid (e.g. maleic acid, fumaric acid).

The compounds (I) and their pharmaceutically acceptable acid addition salts of the present invention have excellent antagonistic activity against histamine with low toxicity and are useful for the prophylaxis and treatment of various allergic diseases induced by histamine, such as allerigoses in respiratory tracts (e.g. allergic rhinitis, allergic inflammatory in respiratory tracts, bronchial asthma), hay fever, allergic dermatoses (e.g. urticaria, eczema, dermatitis, pruritus, drug eruption, local reactions to insect bite), and allergic conjunctivitis.

The antihistaminic activities and acute toxicity of the compounds of the present invention were experimented as follows.

1. Protecting activity against histamine-induced lethality:

Test Compounds (1) Twelve compounds as obtained in Examples 1 to 12 as disclosed hereinafter (the compounds of the present invention)

(2) Chlorpheniramine maleate (reference compound)

(3) Homochlorcyclizine hydrochloride (reference compound)

(4) Compound A, i.e. 1-(4-fluorobenzyl)-2-[4-(2-hydroxyethyl)-1-piperazinyl]methylbenzimidazole (which is disclosed in U.S. Pat. No. 3,423,413) (reference compound)

Test method

The test was carried out by a method similar to Labelle-Tislow method [cf. J. Pharmacol. Exp. Ther., 113, 72, 1955]. That is, each test compound (in an aqueous solution) or distilled water (as control) was orally administered to Hartley strain male and female guinea pigs, weighing 250 to 350 g (one group: 8 animals)

which have been fasted for 20 hours. After one hour, histamine (1.1 mg/kg, in a physiological saline solution) was injected to the animals in cephalic vein. After two hours, the number of live guinea pigs was counted, and therefrom $ED_{50}$ of the compounds was calculated according to Probit method. In the control group (administered with distilled water), all animals died within 5 minutes after injection of histamine due to dyspnea.

Results

The test results are shown in Table 1 together with the acute toxicity.

2. Acute toxicity ($LD_{50}$):

Test compounds

The same compounds as used in the above protecting activity against histamine were used.

Test method

The test compounds (in the form of an aqueous solution or in a suspension in 0.5 % aqueous sodium carboxymethyl cellulose) were orally administered to ddY strain male mice, weighing 20 to 24 g (one group: 3 animals) which have been fasted overnight. The mice were observed for one week as to life or death. The $LD_{50}$ was calculated based on the number of dead mice within one week according to Weil's method (cf. J. Biometric Soc., 8, 249, 1959).

Results

The results are shown in Table 1.

TABLE 1

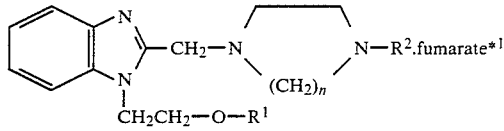

| Test compounds | | | Protecting activity against histamine $ED_{50}$ (mg/kg) | Acute Toxicity $LD_{50}$ (mg/kg) |
|---|---|---|---|---|
| Ex. No. | n | $R^1$ | $R^2$ | | |
| 1 | 2 | —CH₂CH₃ | —H | 0.0033 | >2000 |
| 2 | 3 | —CH₂CH₃ | —H | 0.014 | 1539 |
| 3 | 2 | —CH₂CH₃ | —CH₃ | 0.0026 | 789 |
| 4 | 3 | —CH₂CH₃ | —CH₃ | 0.0092 | 990 |
| 5 | 2 | —CH₂CH₃ | —CH₂CH₃ | 0.0067 | 904 |
| 6 | 2 | —CH₂CH₃ | —CH₂CH₂CH₃ | 0.0095 | 303 |
| 7 | 2 | —CH₂CH₃ | —CH₂CH₂OH | 0.0040 | >2000 |
| 8 | 2 | —CH₂CH₂CH₃ | —CH₃ | 0.0059 | 1006 |
| 9 | 2 | —CH=CH₂ | —CH₃ | 0.0071 | 698 |
| 10 | 2 | —CH₂CH=CH₂ | —CH₃ | 0.0059 | 657 |
| 11 | 2 | —CH₂C≡CH | —CH₃ | 0.0023 | 891 |
| 12 | 3 | —CH₂C≡CH | —CH₃ | 0.017 | 524 |
| Chlorpheniramine maleate*² | | | | 0.17 | 274 |
| Homochlorcyclizine hydrochloride*³ | | | | 0.26 | 382 |

TABLE 1-continued

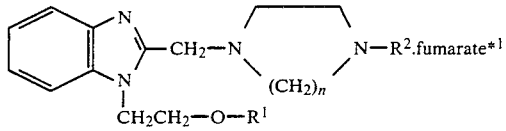

| Test compounds | | | Protecting activity against histamine $ED_{50}$ (mg/kg) | Acute Toxicity $LD_{50}$ (mg/kg) |
|---|---|---|---|---|
| Ex. No. | n | $R^1$ | $R^2$ | | |
| Compound A*⁴ | | | | 0.026 | 440 |

[Remarks]:
*¹Among the test compounds of the present invention, the compound of Example 9 was not in the form of fumarate, but was used in the form of a free base.
*²This compound has the following formula:

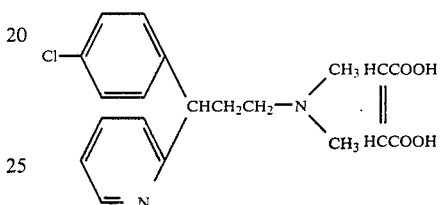

*³This compound has the following formula:

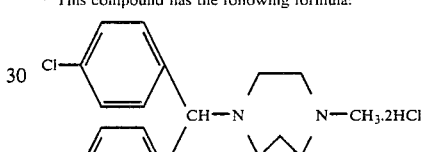

*⁴This compound has the following formula:

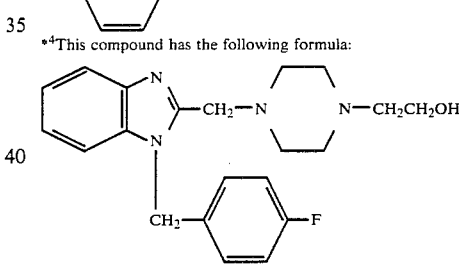

As is clear from the above test results, the compounds of the present invention are superior to the known antihistaminic agents such as chlorpheniramine maleate and homochlorcyclizine hydrochloride of Compound A as disclosed in the above-mentioned literature in the protecting activity against histamine-induced lethality, and further, the compounds of the present invention have generally a large dose in acute toxicity ($LD_{50}$) and hence are also superior to the known compounds in safety.

Besides, the conventional antihistaminics have side-effect such as hypnotic activity. For example, according to the experiment of potentiating effect on hexobarbital-induced sleep in mice, homochlorcyclizine hydrochloride showed remarkable potentiating effect in a dose of 25 mg/kg (p.o.), but for example, the compounds of Examples 1 to 9 and 12 of the present invention did not show such potentiating effect in a dose of 50 mg/kg (p.o.).

The compounds of the present invention, in the form of a free base or a pharmaceutically acceptable acid addition salt thereof, are used for the prophylaxis and treatment of various allergic diseases induced by histamine in conventional preparations for oral administration, injection or external use.

For oral administration, the compounds (I) or their pharmaceutically acceptable acid addition salts are prepared in the conventional dosage forms, for example, solid preparations such as tablets, granules, fine granules, powders, capsules, and liquid preparations such as syrups. The solid preparations are prepared by using conventional pharmaceutically acceptable carriers such as lactose, starches, crystalline cellulose, talc, etc. Capsules are prepared by encapsulating the fine granules or powders containing the active compounds with an appropriate encapsulating agent. Syrups are prepared by dissolving or suspending the active compounds of the present invention in an aqueous solution containing sucrose, carboxymethyl cellulose, etc. The preparations for injection can be prepared by dissolving the pharmaceutically acceptable acid addition salts of the present compounds in distilled water or physiological saline solution. Ointments are prepared by using conventional ointment bases such as vaseline, polyethylene glycol, etc. Intranasal preparations are prepared by dissolving the pharmaceutically acceptable acid addition salts of the present compounds in distilled water or physiological saline solution.

Dose of the present compounds may vary depending on the kinds and severity of diseases, weight and age of patients, etc., but is usually in the range of 0.5 to 5 mg (as a free base) per day in adult in case of oral or injection administration, which is divided in two or three times per day. For external use (e.g. in the form of ointment or intranasal preparation), an appropriate amount of the preparations is applied to the area suffered from the diseases.

The present invention is illustrated by the following Examples and Reference Examples but should not be construed to be limited thereto.

REFERENCE EXAMPLE 1

Preparation of N-(2-ethoxyethyl)-o-nitroaniline (in the formula (VII), $R^1$=ethyl group):

A mixture of o-nitrochlorobenzene (30 g) and 2-ethoxyethylamine (51 g) is stirred at 130° C. for 3 hours. After allowing to cool, ethyl acetate (150 ml) is added to the reaction mixture, and the ethyl acetate layer is separated, washed three times with saturated aqueous saline, dried over anhydrous magnesium sulfate, and then concentrated. The residue is distilled under reduced pressure to give N-(2-ethoxyethyl)-o-nitroaniline (42.9 g) as a reddish brown liquid, b.p. 144°–145.5° C./1.0 mmHg.

Elementary analysis for $C_{10}H_{14}N_2O_3$: Calcd (%): C,57.13; H,6.71; N, 13.32; Found (%): C,57.21; H,6.84; N,13.26.

NMR (CDCl$_3$, δppm): 1.25 (t,3H), 3.3–3.8 (6H), 6.4–6.9 (2H), 7.2–7.5 (1H), 8.08 (dd, 1H), 8.15 (bs. 1H)

REFERENCE EXAMPLE 2

Preparation of N-(2-ethoxyethyl)-o-phenylenediamine (in the formula (VIII), $R^1$=ethyl group):

N-(2-Ethoxyethyl)-o-nitroaniline (42.9 g) obtained in same manner as described in Reference Example 1 is dissolved in ethanol (100 ml), and thereto is added 2.5N aqueous sodium hydroxide (30 ml). To the mixture is added slowly zinc powder (52 g) over a period of 15 minutes while refluxing with gentle stirring. The mixture is refluxed with stirring for 2 hours, and thereafter, the reaction mixture is filtered under heating. The filtrate is concentrated, and to the residue is added ethyl acetate (150 ml). The ethyl acetate layer is separated, washed with saturated aqueous saline, dried over anhydrous magnesium sulfate and then concentrated. The residue is distilled under reduced pressure to give N-(2-ethoxyethyl)-o-phenylenediamine (36.5 g) as a brown liquid, b.p. 122°–124° C./0.85 mmHg.

Elementary analysis for $C_{10}H_{16}N_2O$: Calcd (%): C,66.64; H,8.95; N,15.54; Found (%): C,66.57; H,9.07; N,15.39.

NMR (CDCl$_3$, δppm): 1.15 (t, 3H), 3.05–3.7 (9H), 6.4–6.75 (4H)

REFERENCE EXAMPLE 3

Preparation of 2-chloromethyl-1-(2-ethoxyethyl)benzimidazole (in the formula (II), $R^1$=ethyl group, X=chlorine atom):

N-(2-Ethoxyethyl)-o-phenylenediamine (6.0 g) obtained in the same manner as described in Reference Example 2 is dissolved in 4N hydrochloric acid (60 ml), and thereto is added monochloroacetic acid (4.5 g), and the mixture is refluxed with stirring for 4 hours. After allowing to cool, the reaction mixture is neutralized with aqueous ammonia and then extracted with ethyl acetate (50 ml). The extract is washed with water, dried over anhydrous magnesium sulfate and then concentrated to give a residue (6.5 g). This residue is subjected to silica gel (50 g) column chromatography and eluted with a mixture of cyclohexane-ethyl acetate (3:1 by v/v). The eluate is concentrated to give 2-chloromethyl-1-(2-ethoxyethyl)benzimidazole (3.75 g) as a colorless columns (recrystallized from methanol-water), m.p. 75.5°–77° C.

Elementary analysis for $C_{12}H_{15}N_2OCl$: Calcd (%): C,60.38; H,6.33; N,11.73; Found (%): C,60.45; H,6.33; N,11.78.

NMR (CDCl$_3$, δppm): 1.05 (t, 3H), 3.3 (q, 2H), 3.65 (t, 2H), 4.35 (t, 2H), 4.85 (s, 2H), 7.0–7.25 (3H), (7.45–7.7 (1H).

REFERENCE EXAMPLE 4

Preparation of 2-(4-methyl-1-piperazinyl)methylbenzimidazole (in the formula (X), $R^3$=methyl group, n=2):

N-Methylpiperazine (15 g) is dissolved in ethanol (70 ml), and to the solution is added dropwise a solution of 2-chloromethylbenzimidazole (10 g) in a mixed solvent of ethanol (100 ml)-N,N-dimethylformamide (25 ml) at 60° C. with stirring over a period of 4 hours. After the addition, the mixture is stirred at 60° C. for 2 hours. The reaction mixture is concentrated, and to the residue is added saturated aqueous saline (50 ml) and 5N aqueous sodium hydroxide (40 ml), and the mixture is extracted with chloroform. The extract is washed with saturated aqueous saline, dried over anhydrous magnesium sulfate and then concentrated to give a brown solid material (11.4 g). This solid material is recrystallized from ethyl acetate to give 2-(4-methyl-1-piperazinyl)methylbenzimidazole (4.24 g) as pale yellow needles, m.p. 179°–183° C.

Elementary analysis for $C_{13}H_{18}N_4$: Calcd (%): C,67.80; H,7.88; N,24.33; Found (%): C,67.79; H,8.08; N,24.28.

NMR (CDCl$_3$, δppm): 2.25 (s, 3H), 2.3–2.75 (8H), 3.82 (s, 2H), 7.15–7.4 (2H), 7.45–7.7 (2H)

REFERENCE EXAMPLE 5

Preparation of 2-(4-methyl-1-homopiperazinyl)methylbenzimidazole (in the formula (X), $R^3$=methyl group, n=3):

In the same manner as described in Reference Example 4, N-methylhomopiperazine (15 g) and 2-chloromethylbenzimidazole (10 g) are reacted, and the crude crystal thus obtained is recrystallized from toluene to give 2-(4-methyl-1-homopiperazinyl)methylbenzimidazole (3.81 g) as pale yellow prisms, m.p. 152°–155° C.

Elementary analysis for $C_{14}H_{20}N_4$: Calcd (%): C,68.82; H,8.25; N,22.93; Found (%): C,68.48; H,8.57; N,22.68.

NMR (CDCl$_3$, δppm): 1.6–2.1 (2H), 2.35 (s, 3H), 2.5–2.95 (8H), 3.9 (s, 2H), 7.0–7.3 (2H), 7.35–7.7 (2H)

REFERENCE EXAMPLE 6

Preparation of 2-(4-benzyl-1-piperazinyl)methylbenzimidazole (in the formula (XIV), $R^4$=benzyl group, n=2):

In the same manner as described in Reference Example 4, N-benzylpiperazine (20 g) and 2-chloromethylbenzimidazole (9.0 g) are reacted, and the crude crystal thus obtained is recrystallized from ethyl acetate to give 2-(4-benzyl-1-piperazinyl)methylbenzimidazole (13.8 g) as pale yellow needles, m.p. 195°–201° C.

Elementary analysis for $C_{19}H_{22}N_4$: Calcd (%): C,74.48; H,7.24; N,18.28; Found (%): C,74.55; H,7.32; N,18.16.

NMR (CDCl$_3$, δppm): 2.25–2.7 (8H), 3.45 (s, 2H), 3.75 (s, 2H). 7.05–7.7 (9H)

REFERENCE EXAMPLE 7

Preparation of 2-(4-formyl-1-piperazinyl)methylbenzimidazole (in the formula (XIV), $R^4$=formyl group, n=2):

In the same manner as described in Reference Example 4, N-formylpiperazine (17 g) and 2-chloromethylbenzimidazole (9.0 g) are reacted, and the crude crystal thus obtained is recrystallized from ethyl acetate to give 2-(4-formyl-1-piperazinyl)methylbenzimidazole (10.3 g) as pale yellow flakes, m.p. 194.5°–197.5° C.

Elementary analysis for $C_{13}H_{16}N_4O$: Calcd (%): C,63.92 H,6.60; N,22.93; Found (%): C,63.68; H,6.58; N,22.73.

NMR (CDCl$_3$, δppm): 2.35–2.7 (4H), 3.2–3.65 (4H), 3.9 (s, 2H), 7.15–7.4 (2H), 7.45–7.75 (2H), 8.05 (s, 1H)

EXAMPLE 1

Preparation of 1-(2-ethoxyethyl)-2-(1-piperazinyl(methylbenzimidazole (Process A):

Piperazine (10.9 g) is dissolved in dioxane (100 ml), and thereto is added dropwise with stirring 2-chloromethyl-1-(2-ethoxyethyl)benzimidazole (3.0 g) obtained in the same manner as described in Reference Example 3 in the form of a solution in dioxane (50 ml) over a period of 30 minutes. After completion of the addition, the mixture is stirred at 50° C. for 2 hours. After allowing to cool, the reaction mixture is filtered, and the filtrate is concentrated. To the residue is added saturated aqueous saline (50 ml), and the mixture is adjusted to pH 10 with aqueous sodium hydroxide and then extracted with chloroform. The extract is washed with saturated aqueous saline, dried over anhydrous magnesium sulfate and then concentrated to give a residue (4.8 g). The residue is subjected to silica gel (40 g) column chromatography and eluted with a mixed solvent of chloroform-methanol (2:1 by v/v). The eluate is concentrated to give 1-(2-ethoxyethyl)-2-(1-piperazinyl)methylbenzimidazole (3.37 g) as a pale yellow liquid. This liquid (1.5 g) is dissolved in ethanol (2 ml), and the solution is added to a solution of fumaric acid (0.6 g) in hot ethanol (7.5 ml), and the mixture is allowed to cool. The crude crystal thusobtained is recrystallized from ethanol to give 1-(2-ethoxyethyl)-2-(1-piperazinyl)methbenzimidazole monofumarate monohydrate (1.11 g) as colorless flakes, m.p. 158.5° C. (decomp.)

Elementary analysis for $C_{16}H_{24}N_4O \cdot C_4H_4O_4 \cdot H_2O$: Calcd (%): C,56.86; H,7.16; N,13.26; Found (%): C,56.49; H,7.01; N,13.15.

NMR (DMSO-d$_6$, δppm): 1.0 (t, 3H), 2.35–3.1 (8H), 3.35 (q, 2H), 3.55–3.9 (4H), 4.25–4.6 (2H), 6.4 (s, 2H), 6.95–7.25 (2H). 7.3–7.6 (2H)

The free base of the above compound has the following NMR (CDCl$_3$, δppm):

1.1(t, 3H), 2.1(s, 1H), 2.3–2.6(4H), 2.7–2.95(4H), 3.35(q, 2H), 3.7(t, 2H), 3.75(s, 2H), 4.45(t, 2H), 7.0–7.35(3H), 7.45–7.7(1H)

EXAMPLE 2

Preparation of 1-(2-ethoxyethyl)-2-(1-homopiperazinyl)methylbenzimidazole (Process A):

In the same manner as described in Example 1, homopiperazine (8.0 g) and 2-chloromethyl-1-(2-ethoxyethyl)benzimidazole (2.4 g) obtained in the same manner as described in Reference Example 3 are reacted to give 1-(2-ethoxyethyl)-2-(1-homopiperazinyl)methylbenzimidazole (2.0 g) as a pale yellow liquid. This liquid is treated with fumaric acid (1.15 g,), and the crude crystal thus obtained is recrystallized from a mixed solvent of ethyl acetate-ethanol to give 1-(2-ethoxyethyl)-2-(1-homopiperazinyl)methylbenzimidazole 3/2 fumarate (1.75 g) as colorless prisms, m.p. 151°–152° C.

Elementary analysis for $C_{17}H_{26}N_4O \cdot 3/2 C_4H_4O_4$: Calcd (%): C,57.97; H,6.77; N,11.76; Found (%): C,58.24; H,6.97; N,11.82.

NMR (DMSO-d$_6$, δppm): 1.0 (t, 3H), 1.6–2.1 (2H), 2.6–3.55 (10H), 3.6–3.85 (2H), 3.95 (s, 2H), 4.35–4.6 (2H), 6.5 (s, 3H), 7.05–7.3 (2H), 7.4–7.7 (2H)

The free base of the above compound has the following NMR (CDCl$_3$, δppm):

1.1 (t, 3H), 1.5–1.95 (2H), 2.6–3.05 (9H), 3.4 (q, 2H), 3.75 (t, 2H), 4.0 (s, 2H), 4.55 (t, 2H), 7.1–7.45 (3H), 7.6–7.9 (1H)

EXAMPLE 3

Preparation of 1-(2-ethoxyethyl)-2-(4-methyl-1-piperazinyl)methylbenzimidazole (Process A):

To a solution of 2-chloromethyl-1-(2-ethoxyethyl)-benzimidazole (1.5 g) obtained in the same manner as described in Reference Example 3 in benzene (10 ml) is added dropwise a solution of N-methylpiperazine (1.4 g) in benzene (5 ml) with stirring under ice-cooling over a period of 10 minutes. After completion of the addition, the mixture is stirred under ice-cooling for 2 hours. After allowing to stand at room temperature overnight, the reaction mixture is washed with water, dried over anhydrous magnesium sulfate and then concentrated to give 1-(2-ethoxyethyl)-2-(4-methyl-1-piperazinyl)methylbenzimidazole (1.9 g) as a pale yellow liquid. This liquid is treated with fumaric acid (1.3 g). The crude crystal thus obtained is recrystallized from a mixed solvent of ethyl acetate-ethanol to give 1-(2-ethoxyethyl)-2-(4-methyl-1-piperazinyl)methylbenzimidazole monofumarate semihydrate (1.9 g) as colorless plates, m.p. 155°–160° C.

Elementary analysis for $C_{17}H_{16}N_4O \cdot C_4H_4O_4 \cdot \frac{1}{2}H_2O$: Calcd: (%): C,59.00; H,7.31; N,13.11; Found (%): C,59.27; H,7.29; N,13.01.

NMR (DMSO-$d_6$, δppm): 1.0 (t, 3H), 2.3 (s, 3H), 2.4–2.7 (8H), 3.35 (q, 2H), 3.5–3.8 (4H), 4.25–4.5 (s, 2H), 6.45 (s, 2H), 6.9–7.5 (4H)

The free base of the above compound has the following NMR (CDCl$_3$, δppm):

1.1 (t, 3H), 2.25 (s, 3H), 2.3–2.7 (8H), 3.4 (q, 2H), 3.7 (t, 2H), 3.85 (s, 2H), 4.5 (t, 2H), 7.1–7.4 (3H), 7.55–7.8 (1H)

EXAMPLE 4

Preparation of 1-(2-ethoxyethyl)-2-(4-methyl-1-homopiperazinyl)methylbenzimidazole (Process A):

In the same manner as described in Example 3, N-methylhomopiperazine (2.6 g) and 2-chloromethyl-1-(2-ethoxyethyl)benzimidazole (2.38 g) obtained in the same manner as described in Reference Example 3 are reacted to give 1-(2-ethoxyethyl)-2-(4-methyl-1-homopiperazinyl)methylbenzimidazole (2.2 g) as a pale yellow liquid. This liquid is treated with fumaric acid (1.63 g), and the crude crystal thus obtained is recrystallized from a mixed solvent of ethyl acetate-ethanol to give 1-(2-ethoxyethyl)-2-(4-methyl-1-homopiperazinyl)methylbenzimidazole 3/2 fumarate semihydrate (2.2 g) as colorless prisms, m.p. 119°–121.5° C.

Elementary analysis for $C_{23}H_{28}N_4O \cdot 3/2 C_4H_4O_4 \cdot \frac{1}{2}H_2O$: Calcd (%): C,57.50; H,7.06; N,11.22; Found (%): C,57.63; H,7.13; N,11.30.

NMR (DMSO-$d_6$, δppm): 1.0 (t, 3H), 1.7–2.15 (2H), 2.55–3.25 (11H), 3.35 (q, 2H), 3.55–3.8 (2H), 3.95 (s, 2H), 4.3–4.6 (2H), 6.45 (s, 3H), 6.95–7.2 (2H), 7.3–7.55 (2H)

The free base of the above compound has the following NMR (CDCl$_3$, δppm):

1.1 (t, 3H), 1.55–2.1 (2H), 2.3 (s, 3H), 2.45–2.9 (8H), 3.36 (q, 2H), 3.7 (t, 2H), 3.95 (s, 2H), 4.5 (t, 2H), 7.05–7.3 (3H), 7.5–7.75 (1H)

EXAMPLE 5

Preparation of 1-(2-ethoxyethyl)-2-(4-ethyl-1-piperazinyl)methylbenzimidazole (Process A'):

A mixture of 1-(2-ethoxyethyl)-2-(1-piperazinyl)methylbenzimidazole (1.58 g) obtained in the same manner as described in Example 1, ethyl iodide (1.03 g) and potassium carbonate (0.83 g) in ethanol (20 ml) is refluxed with stirring for 3 hours. The reaction mixture is concentrted, and to the residue is added saturated aqueous saline (30 ml) and the mixture is extracted with ethyl acetate (50 ml). The extract is washed with water, dried over anhydrous magnesium sulfate and then concentrated to give a yellow liquid (1.8 g). This liquid is subjected to silica gel (20 g) column chromatography and eluted with a mixed solvent of chloroform-methanol (10:1 by v/v). The eluate is concentrated to give 1-(2-ethoxyethyl)-2-(4-ethyl-1-piperazinyl)methylbenzimidazole (1.6 g) as a pale yellow liquid. This liquid is treated with fumaric acid (0.87 g), and the crude crystal thus obtained is recrystallized from ethanol to give 1-(2-ethoxyethyl)-2-(4-ethyl-1-piperazinyl)methylbenzimidazole 3/2 fumarate (1.84 g) as colorless needles, m.p. 182°–183° C.

Elementary analysis for $C_{18}H_{28}N_4O \cdot 3/2 C_4H_4O_4$: Calcd (%): C,58.76; H,6.99; N,11.42; Found (%): C,58.80; H,7.00; N,11.36.

NMR (DMSO-$d_6$, δppm): 0.75 (t, 3H), 0.85 (t, 3H), 2.2–2.7 (10H), 3.15 (q, 2H), 3.35–3.7 (4H), 4.1–4.4 (2H), 6.4 (s, 3H), 6.9–7.15 (2H), 7.25–7.5 (2H)

The free base of the above compound has the following NMR (CDCl$_3$, δppm):

1.05 (t, 3H), 1.1 (t, 3H), 2.2–2.7 (10H), 3.35 (q, 2H), 3.7 (t, 2H), 3.8 (s, 2H), 4.4 (t, 2H), 7.0–7.35 (3H), 7.45–7.7 (1H)

EXAMPLE 6

Preparation of 1-(2-ethoxyethyl)-2-(4-n-propyl-1-piperazinyl)methylbenzimidazole (Process A'):

A mixture of 1-(2-ethoxyethyl)-2-(1-piperazinyl)methylbenzimidazole (3.1 g) obtained in the same manner as described in Example 1, n-propyl bromide (2.0 g) and potassium carbonate (2.25 g) in ethanol (60 ml) is refluxed with stirring for 6.5 hours. The reaction mixture is treated in the same manner as described in Example 5 and the crude product is purified likewise to give 1-(2-ethoxyethyl)-2-(4-n-propyl-1-piperazinyl)methylbenzimidazole (3.1 g) as a pale brown liquid. This liquid is treated with fumaric acid (2.0 g), and the crude crystal thus obtained is recrystallized from ethanol to give 1-(2-ethoxyethyl)-2-4-n-propyl-1-piperazinyl)methylbenzimidazole 3/2 fumarate (3.9 g) as colorless needles, m.p. 178.5°–180° C.

Elementary analysis for $C_{19}H_{30}N_4O \cdot 3/2 C_4H_4O_4$: Calcd (%): C,59.51; H,7.19; N,11.10; Found (%): C,59.51; H,7.35; N,11.13.

NMR (DMSO-$d_6$, δppm): 0.7–1.2 (6H), 1.2–1.8 (2H), 2.3–2.9 (10H), 3.15–4.0 (6H), 4.3–4.6 (2H), 6.55 (s, 3H), 7.0–7.35 (2H), 7.35–7.7 (2H)

The free base of the above compound has the following NMR (CDCl$_3$, δppm):

0.75–1.8 (8H), 2.15–2.7 (10H), 3.35 (q, 2H), 3.7 (t, 2H), 3.8 (s, 2H), 4.45 (t, 2H), 7.0–7.35 (3H), 7.5–7.75 (1H)

EXAMPLE 7

Preparation of 1-(2-ethoxyethyl)-2-[4-(2-hydroxyethyl)-1-piperazinyl]methylbenzimidazole (Process A):

In the same manner as described in Example 3, 2-chloromethyl-1-(2-ethoxyethyl)benzimidazole (3.5 g) obtained in the same manner as described in Reference Example 3 and N-(2-hydroxyethyl)piperazine (4.9 g) are reacted to give 1-(2-ethoxyethyl-2-[4-(2-hydroxyethyl)-1-piperazinyl]methylbenzimidazole (5.0 g) as a pale brown liquid. This liquid is treated with fumaric acid (3.5 g), and the crude crystal thus obtained is recrystallized from ethanol to give 1-(2-ethoxyethyl)-2-[4-(2-hydroxyethyl)-1-piperazinyl[methylbenzimidazole 3/2 fumarate (5.3 g) as colorless needles, m.p. 160°–160.5° C.

Elementary analysis for $C_{18}H_{28}N_4O_2 \cdot 3/2 C_4H_4O_4$: Calcd (%): C,56.91; H,6.76; N,11.06; Found (%): C,56.86; H,6.91; N,11.00.

NMR (DMSO-$d_6$, δppm): 1.05 (t, 3H), 2.4–2.9 (10H), 3.4 (q, 2H), 3.5–3.9 (6H), 4.35–4.6 (2H), 6.6 (s, 3H), 7.05–7.3 (2H), 7.4–7.7 (2H)

The free base of the above compound has the following NMR (CDCl$_3$, δppm):

1.1 (t, 3H), 2.3–2.7 (10H), 3.15–3.85 (9H), 4.4 (t, 2H), 6.95–7.3 (3H), 7.45–7.7 (1H)

EXAMPLE 8

Preparation of 1-(2-n-propoxyethyl)-2-(4-methyl-1-piperazinyl)methylbenzimidazole (Process B):

2-(4-Methyl-1-piperazinyl)methylbenzimidazole (4.0 g) obtained in the same manner as described in Reference Example 4 and 2-bromoethyl n-propyl ether (4.0 g) are dissolved in N,N-dimethylformamide (30 ml), and thereto is added sodium hydride (50% in oil) (1.0 g), and the mixture is stirred at 60° C. for 2 hours. To the reaction mixture is added water (100 ml), and the mixture is extracted with ethyl acetate (salting out). The extract is washed four times with water, dried over anhydrous magnesium sulfate and then concentrated to give 1-(2-n-propoxyethyl)-2-(4-methyl-1-piperazinyl)methylbenzimidazole (4.89 g) as a pale yellow solid. A part of this solid is recrystallized from n-hexane to give colorless needles, m.p. 73°–75.5° C.

Elementary analysis for $C_{18}H_{28}N_4O$: Calcd (%): C,68.32; H,8.92; N,17.71; Found (%): C,68.86; H,8.88; N,17.75;

NMR (CDCl$_3$, δppm): 0.85 (t, 3H), 1.25–1.8 (m, 2H), 2.3 (s, 3H), 2.3–2.7 (8H), 3.35 (t, 2H), 3.8 (t, 2H), 3.9 (s, 2H), 4.55 (t, 2H), 7.2–7.5 (3H), 7.65–7.9 (1H)

The above-obtained pale yellow solid [i.e. 1-(2-n-propoxyethyl)-2-(4-methyl-1-piperazinyl)methylbenzimidazole] (3.5 g) is treated with fumaric acid (2.57 g), and the crude crystal thus obtained is recrystallized from ethyl acetate-ethanol to give 1-(2-n-propoxyethyl)-2-(4-methyl-1-piperaziny)methylbenzimidazole difumarate (3.49 g) as colorless crystals, m.p. 160.5°–161.5° C.

Elementary analysis for $C_{18}H_{28}N_4O \cdot 2C_4H_4O_4$: Calcd (%): C,56.92; H,6.61; N,10.21; Found (%): C,56.84; H,6.56; N,10.23.

NMR (DMSO-d$_6$, δppm): 0.75 (t, 3H), 1.1–1.6 (m, 2H), 2.35–3.0 (11H), 3.25 (t, 2H), 3.55–3.9 (4H), 4.35–4.6 (2H), 6.6 (s, 4H), 7.05–7.3 (m, 2H), 7.4–7.65 (m, 2H)

EXAMPLE 9

Preparation of 1-(2-vinyloxyethyl)-2-(4-methyl-1-piperazinyl)methylbenzimidazole (Process B):

2-(4-Methyl-1-piperazinyl)methylbenzimidazole (4.0 g) obtained in the same manner as described in Reference Example 4, 2-chloroethyl vinyl ether (3.0 g) and sodium hydride (50% in oil) (1.0 g) are dissolved in N,N-dimethylformamide (35 ml), and the mixture is stirred at 60° C. for 3.5 hours. The reaction mixture is treated in the same manner as described in Example 8 to give a brown liquid (4.82 g). This liquid is subjected to silica gel (70 g) column chromatography and eluted with chloroform-methanol (30:1 by v/v). The eluate is concentrated to give 1-(2-vinyloxyethyl)-2-(4-methyl-1-piperazinyl)methylbenzimidazole (2.92 g) as pale yellow solid. This is recrystallized from ether-hexane to give colorless prisms, m.p. 65.5°–67.5° C.

Elementary analysis for $C_{17}H_{24}N_4O$: Calcd (%): C,67.97; H,8.05; N,18.65; Found (%): C,68.11; H,8.04; N,18.61.

NMR (CDCl$_3$, δppm): 2.25 (s, 3H), 2.25–2.7 (8H), 3.83 (s, 2H), 3.85–4.3 (4H), 4.45–4.7 (2H), 6.38 (dd, 1H), 7.15–7.45 (3H), 7.6–7.85 (1H)

EXAMPLE 10

Preparation of 1-(2-allyloxyethyl)-2-(4-methyl-1-piperazinyl)methylbenzimidazole (Process B):

2-(4-Methyl-1-piperazinyl)methylbenzimidazole (2.3 g) obtained in the same manner as described in Reference Example 4, allyl 2-bromoethyl ether (2.5 g) and sodium hydride (50% in oil) (1.0 g) are dissolved in N,N-dimethylformamide (30 ml), and the mixture is stirred at room temperature for 5 hours. The reaction mixture is treated in the same manner as described in Example 8 to give a yellow liquid (2.4 g). This liquid is subjected to silica gel (40 g) column chromatography and eluted with chloroform-methanol (7:1 by v/v). The eluate is concentrated to give 1-(2-allyloxyethyl)-2-(4-methyl-1-piperazinyl)methylbenzimidazole (1.74 g) as a pale yellow liquid. This liquid is treated with fumaric acid (0.96 g), and the crude crystal thus obtained is recrystallized from ethanol to give 1-(2-allyloxyethyl)-2-(4-methyl-1-piperazinyl)methylbenzimidazole monofumarate 1.5 hydrate (1.30 g) as pale yellow needles, m.p. 166° C. (decomp.).

Elementary analysis for $C_{18}H_{26}N_4O \cdot C_4H_4O_4 \cdot 3/2 H_2O$ Calcd (%): C,57.75; H, 7.27; N,12.25 Found (%): C,57.21; H,7.12; N,12.14.

NMR (DMSO-d$_6$, δppm): 2.35 (s, 3H), 2.4–2.75 (8H), 3.55–3.95 (6H), 4.3–4.6 (2H), 4.8–5.2 (2H), 5.4–6.2 (1H), 6.5 (s, 2H), 6.95–7.25 (2H), 7.3–7.6 (2H)

The free base of this compound has the following NMR (CDCl$_3$, δppm):

2.2 (s, 3H), 2.3–2.7 (8H), 3.6–3.95 (6H), 4.45 (t, 2H), 4.85–5.25 (2H), 5.4–6.0 (1H), 7.0–7.4 (3H), 7.45–7.7 (1H)

EXAMPLE 11

Preparation of 1-(2-propargyloxyethyl)-2-(4-methyl-1-piperazinyl)methylbenzimidazole (Process B):

2-(4-Methyl-1-piperazinyl)methylbenzimidazole (5.0 g) obtained in the same manner as described in Reference Example 4, 2-bromoethyl propargyl ether (4.8 g) and sodium hydride (50% in oil) (1.5 g) are dissolved in N,N-dimethylformamide (40 ml), and the mixture is stirred at 60° C. for 4 hours. The reaction mixture is treated in the same manner as described in Example 8 to give a brown liquid (6.75 g). This liquid is subjected to silica gel (90 g) column chromatography and eluted with chloroform-methanol (30:1 by v/v). The eluate is concentrated to give 1-(2-propargyloxyethyl)-2-(4-methyl-1-piperazinyl)methylbenzimidazole (1.93 g) as a pale yellow liquid. This liquid is treated with fumaric acid (1.43 g), and the crude crystal thus obtained is recrystallized from ethyl acetate-ethanol to give 1-(2-propargyloxyethyl)-2-(4-methyl-1-piperazinyl)methylbenzimidazole monofumarate semihydrate (1.15 g) as colorless needles, m.p. 159.5°–163° C.

Elementary analysis for $C_{18}H_{24}N_4O \cdot C_4H_4O_4 \cdot \frac{1}{2} H_2O$: Calcd (%): C,60.40; H,6.68; N,12.81; Found (%): C,60.40; H,6.43; N,12.33

NMR (DMSO-d$_6$, δppm): 2.3–2.8 (11H), 3.35 (t, 1H), 3.65–3.9 (4H), 4.1 (d, 2H), 4.5 (t, 2H), 6.6 (s, 2H), 7.1–7.3 (2H), 7.4–7.65 (2H)

The free base of this compound has the following NMR (CDCl$_3$, δppm):

2.25 (s, 3H), 2.3–2.7 (9H), 3.75–4.0 (4H), 4.07 (d, 2H), 4.55 (t, 2H), 7.1–7.45 (3H), 7.6–7.85 (1H)

EXAMPLE 12

Preparation of 1-(2-propargyloxyethyl)-2-(4-methyl-1-homopiperazinyl)methylbenzimidazole (Process B):

2-(4-Methyl-1-homopiperazinyl)methylbenzimidazole (2.5 g) obtained in the same manner as described in Reference Example 5, 2-bromoethyl propargyl ether (2.5 g) and sodium hydride (50% in oil) (0.7 g) are dissolved in N,N-dimethylformamide (45 ml), and the mixture is stirred at 60° C. for 3 hours. The reaction mixture is treated in the same manner as described in Example 8 to give a brown liquid (2.5 g). This liquid is subjected to silica gel (50 g) column chromatography and eluted with chloroform-methanol (6:1 by v/v). The eluate is concentrated to give 1-(2-propargyloxyethyl)-2-(4-methyl-1-homopiperazinyl)methylbenzimidazole (1.5 g) as a pale yellow liquid. This liquid is treated with fumaric acid (1.1 g), and the crude crystal thus obtained is recrystallized from ethyl acetate-ethanol to give 1-(2-propargyloxyethyl)-2-(4-methyl-1-homopiperazinyl)-methylbenzimidazole 3/2 fumarate (0.8 g) as colorless prisms, m.p. 133°–136° C.

Elementary analysis for $C_{19}H_{26}N_4O.3/2C_4H_4O_4$: Calcd (%): C,59.99; H,6.44; N,11.19; Found (%): C,59.98; H,6.52; N,11.36.

NMR (DMSO-$d_6$, δppm): 1.8–2.2 (2H), 2.6–3.3 (11H), 3.35 (t, 1H), 3.65–4.0 (4H), 4.1 (d, 2H), 4.4–4.65 (2H), 6.55 (s, 3H), 7.05–7.3 (2H), 7.4–7.65 (2H)

The free base of this compound has the following NMR (CDCl$_3$, δppm):

1.55–2.0 (2H), 2.3 (s, 3H), 2.35 (t, 1H), 2.45–2.85 (8H), 3.8 (t, 2H), 3.9 (s, 2H), 4.0 (d, 2H), 4.5 (t, 2H), 7.0–7.3 (3H), 7.5–7.7 (1H)

EXAMPLE 13

Preparation of 1-(2-ethoxyethyl)-2-(1-piperazinyl)methylbenzimidazole (Process B):

(1) 2-(4-Benzyl-1-piperazinyl)methylbenzimidazole (4.0 g) obtained in the same manner as described in Reference Example 6, 2-bromoethyl ethyl ether (3.0 g) and sodium hydride (50% in oil) (1.0 g) are dissolved in N,N-dimethylformamide (25 ml), and the mixture is stirred at 60° C. for 8 hours. The reaction mixture is treated in the same manner as described in Example 8 to give a brown liquid (4.75 g). This liquid is subjected to silica gel (70 g) column chromatography and eluted with chloroform-methanol (20:1 by v/v). The eluate is concentrated to give 1-(2-ethoxyethyl)-2-(4-benzyl-1-piperazinyl)methylbenzimidazole (4.15 g) as a brown liquid.

NMR (CDCl$_3$, δppm): 1.1 (t, 3H), 2.3–2.7 (8H), 3.4 (q, 2H), 3.5 (s, 2H), 3.75 (t, 2H), 3.85 (s, 2H), 4.5 (s, 2H), 7.15–7.45 (8H), 7.6–7.9 (1H)

(2) 1-(2-Ethoxyethyl)-2-(4-benzyl-1-piperazinyl)methylbenzimidazole (3.0 g) obtained in the above (1) is dissolved in isopropyl alcohol (15 ml) and 2.5N hydrochloric acid (12 ml), and thereto is added palladium black (0.45 g), and the mixture is subjected to catalytic hydrogenation at 40° C. under 3 atm. for 13.5 hours. The reaction mixture is filtered, and the filtrate is concentrated. To the residue is added 5N aqueous sodium hydroxide (20 ml), and the mixture is extracted with chloroform. The extract is dried over anhydrous magnesium sulfate and then concentrated to give a residue (1.83 g). This residue is subjected to silica gel (20 g) column chromatography and eluted with chloroform-methanol (7:1 by v/v), and the eluate is concentrated to give 1-(2-ethoxyethyl)-2-(1-piperazinyl)methylbenzimidazole (1.09 g) as a pale yellow liquid. This liquid has the same NMR spectrum as that of the free base obtained in Example 1.

EXAMPLE 14

Preparation of 1-(2-ethoxyethyl)-2-(1-piperazinyl)methylbenzimidazole (Process B):

(1) 2-(4-Formyl-1-piperazinyl)methylbenzimidazole (3.5 g) obtained in the same manner as described in Reference Example 7, 2-bromoethyl ethyl ether (3.5 g) and sodium hydride (50% in oil) (1.0 g) are dissolved in N,N-dimethylformamide (25 ml), and the mixture is stirred at 60° C. for 2 hours. The reaction mixture is treated in the same manner as described in Example 8 to give a brown liquid (3.06 g). This liquid is subjected to silica gel (55 g) column chromatography and eluted with chloroform-methanol (20:1 by v/v). The eluate is concentrated to give 1-(2-ethoxyethyl)-2-(4-formyl-1-piperazinyl)methylbenzimidazole (2.66 g) as a yellow liquid.

NMR (CDCl$_3$, δppm): 1.1 (t, 3H), 2.35–2.7 (4H), 3.2–3.85 (8H), 3.9 (s, 2H), 4.5 (t, 2H), 7.15–7.45 (3H), 7.6–7.85 (1H), 8.05 (s, 1H)

(2) 1-(2-Ethoxyethyl)-2-(4-formyl-1-piperazinyl)methylbenzimidazole (1.0 g) obtained in the above (1) is added to 20% aqueous sodium hydroxide (3 ml), and the mixture is stirred at 100° C. for 15.5 hours. To the reaction mixture is added water (20 ml), and the mixture is extracted with chloroform. The extract is dried over anhydrous magnesium sulfate and then concentrated to give a residue (0.78 g). This residue is subjected to silica gel (20 g) column chromatography and eluted with chloroform-methanol (7:1 by v/v), and the eluate is concentrated to give 1-(2-ethoxyethyl)-2-(1-piperazinyl)methylbenzimidazole (0.51 g) as a pale yellow liquid. This liquid has the same NMR spectrum as that of the free base obtained in Example 1.

EXAMPLE 15

Preparation of tablets:

There are prepared tablets containing as an active ingredient 1-(2-ethoxyethyl)-2-(1-piperazinyl)methylbenzimidazole monofumarate monohydrate (the compound of Example 1) (0.5 mg per each tablet) according to the following formulation:

| Ingredients | Amount (g) |
|---|---|
| Compound of Example 1 | 10 |
| Crystalline cellulose | 1610 |
| Lactose | 1600 |
| Calcium carboxymethyl cellulose | 120 |
| Talc | 40 |
| Magnesium stearate | 20 |

The above ingredients are homogeneously mixed, and the mixture is tabletted in a conventional manner to give tablets (weight of each tablet: 170 mg).

EXAMPLE 16

Preparation of powders:

There are prepared powders containing as an active ingredient 1-(2-ethoxyethyl)-2-[4-(2-hydroxyethyl)-1-piperazinyl]methylbenzimidazole 3/2 fumarate (the compound of Example 7) (0.5 mg per each folded powder) according to the following formulation:

| Ingredients | Amount (g) |
|---|---|
| Compound of Example 7 | 5 |
| Lactose | 595 |
| Starch | 400 |

The above ingredients are homogeneously mixed, and the mixture is folded in powder papers (each content: 100 mg).

EXAMPLE 17

Preparation of capsules:

There are prepared capsules containing as an active ingredient 1-(2-ethoxyethyl)-2-(4-ethyl-1-piperazinyl)-methylbenzimidazole 3/2 fumarate (the compound of Example 5) (0.5 mg per each capsule) according to the following formulation:

| Ingredients | Amount (g) |
| --- | --- |
| Compound of Example 5 | 10 |
| Lactose | 2000 |
| Crystalline cellulose | 910 |
| Talc | 60 |
| Magnesium stearate | 20 |

The above ingredients are homogeneously mixed, and the mixture is packed in 3# hard capsules (each content: 150 mg).

EXAMPLE 18

Preparation of syrups:

There are prepared syrups containing as an active ingredient 1-(2-n-propoxyethyl)-2-(4-methyl-1-piperazinyl)methylbenzimidazole difumarate (the compound of Example 8) (0.2 mg, i.e. 0.02% by weight, per 1 g of the syrup) according to the following formulation:

| Ingredients | Amount (g) |
| --- | --- |
| Compound of Example 8 | 0.4 |
| Sucrose | 1200 |
| Ethyl p-hydroxybenzoate | 0.4 |
| Propyl p-hydroxybenzoate | 0.2 |
| Purified water | 799 |

In purified water are dissolved other ingredients, and the mixture is homogeneously mixed with stirring to give the syrups.

EXAMPLE 19

Preparation of injections:

There are prepared ampoules for injection containing as an active ingredient 1-(2-ethoxyethyl)-2-(1-piperazinyl)methylbenzimidazole monofumarate monohydrate (the compound of Example 1) (1 mg per each ampoule: 1 ml) according to the following formulation:

| Ingredients | Amount (g) |
| --- | --- |
| Compound of Example 1 | 1 |
| Physiological saline solution | q.s. |
|  | 1000 ml |

EXAMPLE 20

Preparation of ointments:

There are prepared ointments containing as an active ingredient 1-(2-ethoxyethyl)-2-(4-ethyl-1-piperazinyl)-methylbenzimidazole 3/2 fumarate (the compound of Example 5) (5 mg per 1 g of the ointment) according to the following formulation:

| Ingredients | Amount (g) |
| --- | --- |
| Compound of Example 5 | 0.5 |
| Polyethylene glycol 4000 | 49.5 |
| Polyethylene glycol 400 | 50 |

The above ingredients are well mixed, and the mixture is molten with heating, and then allowed to cool to give the ointments.

EXAMPLE 21

Preparation of intranasal preparations:

There are prepared intranasal preparations containing as an active ingredient 1-(2-ethoxyethyl)-2-(4-methyl-1-piperazinyl)methylbenzimidazole monofumarate semihydrate (the compound of Example 3) (1 mg per 1 g of the preparation) according to the following formulation:

| Ingredients | Amount (g) |
| --- | --- |
| Compound of Example 3 | 1 |
| Ethyl p-hydroxybenzoate | 0.5 |
| Physiological saline solution | 998.5 |

The above ingredients are homogeneously mixed to give a solution.

What is claimed is:

1. A benzimidazole compound of the formula $$\text{benzimidazole}\text{-}CH_2\text{-}N\overset{(CH_2)_n}{\underset{CH_2CH_2\text{-}O\text{-}R^1}{\diagup\diagdown}}N\text{-}R^2$$

wherein $R^1$ is a lower alkyl group, a lower alkenyl group or a lower alkynyl group, $R^2$ is hydrogen atom, a lower alkyl group or a lower hydroxyalkyl group, and $n$ is 2 or 3, or a pharmaceutically acceptable acid addition salt thereof.

2. The compound according to claim 1, which is 1-(2-ethoxyethyl)-2-(4-methyl-1-piperazinyl)methylbenzimidazole or a pharmaceutically acceptable acid addition salt thereof.

3. The compound according to claim 1, which is 1-(2-ethoxyethyl)-2-(1-piperazinyl)methylbenzimidazole or a pharmaceutically acceptable acid addition salt thereof.

4. The compound according to claim 1, which is 1-(2-propargyloxyethyl)-2-(4-methyl-1-piperazinyl)methylbenzimidazole or a pharmaceutically acceptable acid addition salt thereof.

5. An antihistaminic composition which comprises as an active ingredient an antihistaminically effective amount of a benzimidazole compound of the formula:

$$\text{benzimidazole}\text{-}CH_2\text{-}N\overset{(CH_2)_n}{\underset{CH_2CH_2\text{-}O\text{-}R^1}{\diagup\diagdown}}N\text{-}R^2$$

wherein $R^1$ is a lower alkyl group, a lower alkenyl group or a lower alkynyl group, $R^2$ is hydrogen atom, a lower alkyl group or a lower hydroxyalkyl group, and $n$ is 2 or 3, or a pharmaceutically acceptable acid addition salt thereof in admixture with a pharmaceutically acceptable carrier or diluent.

6. The composition according to claim 5, wherein the active ingredient is 1-(2-ethoxyethyl)-2-(4-methyl-1- piperazinyl)methylbenzimidazole or a pharmaceutically acceptable acid addition salt thereof.

7. The composition according to claim 5, wherein the active ingredient is 1-(2-ethoxyethyl)-2-(1-piperazinyl)-methylbenzimidazole or a pharmaceutically acceptable acid addition salt thereof.

8. The composition acording to claim 5, wherein the active ingredient is 1-(2-propargyloxyethyl)-2-(4-methyl-1-piperazinyl)methylbenzimidazole or a pharmaceutically acceptable acid addition salt thereof.

* * * * *